United States Patent [19]

Wunder et al.

[11] 4,370,261

[45] Jan. 25, 1983

[54] CARRIER CATALYST FOR THE PREPARATION OF VINYL ACETATE FROM ETHYLENE, ACETIC ACID AND OXYGEN IN THE GASEOUS PHASE

[75] Inventors: Friedrich Wunder, Flörsheim am Main; Therese Quadflieg; Günter Roscher, both of Kelkheim; Günther Heck, Wiesbaden, all of Fed. Rep. of Germany

[73] Assignee: Hoechst Aktiengesellschaft, Frankfurt am Main, Fed. Rep. of Germany

[21] Appl. No.: 20,038

[22] Filed: Mar. 13, 1979

[30] Foreign Application Priority Data

Mar. 15, 1978 [DE] Fed. Rep. of Germany ....... 2811115

[51] Int. Cl.³ .................... B01J 21/08; B01J 23/38; B01J 35/00
[52] U.S. Cl. ................... 252/460; 252/477 R
[58] Field of Search ................... 252/477 R, 460

[56] References Cited

U.S. PATENT DOCUMENTS

| | | | |
|---|---|---|---|
| 2,408,164 | 9/1946 | Foster | 252/477 R |
| 2,644,800 | 7/1953 | Mottern et al. | 252/477 R |
| 3,764,565 | 10/1973 | Jacobs et al. | 252/477 R |
| 3,857,680 | 12/1974 | Porta et al. | 252/477 R |

*Primary Examiner*—Carl F. Dees
*Attorney, Agent, or Firm*—Curtis, Morris & Safford

[57] ABSTRACT

Figure 8:
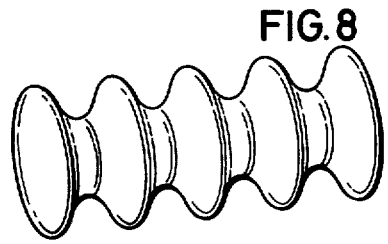

The carriers contain common active components, namely noble metals of the 8th sub-group or compounds thereof, and as activators alkali metal compounds, alkaline earth metal compounds or cadmium compounds. The carriers, too, consist of common materials, such as silicic acid. A novel feature is to be seen in the shape of the carrier particles which are designed as rod sections having a star-shaped cross section (FIGS. 1 to 7) or as ribbed rods (FIG. 8). In relation to the apparent density and thus in relation to the amount of noble metal employed, a considerably higher space-time yield is reached than with carrier particles of a conventional shape.

3 Claims, 8 Drawing Figures

CARRIER CATALYST FOR THE PREPARATION OF VINYL ACETATE FROM ETHYLENE, ACETIC ACID AND OXYGEN IN THE GASEOUS PHASE

It is well-known that ethylene can be reacted with acetic acid and oxygen in the gaseous phase to give vinyl acetate. Suitable catalysts contain a noble metal proportion and an activator proportion. The noble metal proportion consists of noble metals of the 8th sub-group of the Periodic System and/or compounds thereof; in addition, there may also be present elements of the first sub-group and/or their compounds. The activator proportion consists of compounds of elements of the first main group and/or the second main group and/or cadmium. Preference is given to palladium as element of the 8th sub-group, gold as element of the 1st sub-group, and potassium as element of the 1st main group. These active components are applied in a fine distribution onto carriers, while using generally silicic acid or aluminum oxide as carrier material. However, in order to give very high space-time yields, the carrier catalysts must have a relatively high content of palladium and optionally gold, which involves a considerable expenditure. Catalysts in which only the outer layer of the carrier has been impregnated with the active components, only give space-time yields that are generally not above 300 to 500 g of vinyl acetate per liter of catalyst and hour. With catalysts in which the entire carrier material has been impregnated, space-time yields of from 1,000 to 1,200 g/l.h are obtained but with a higher amount of noble metal being required. For the above process which is carried out in many plants on an industrial scale, a catalyst leading to the same or higher space-time yields with a smaller amount of noble metal used would represent a great advantage with regard to economy.

There has now been found a catalyst for the preparation of vinyl acetate in the gaseous phase from ethylene, acetic acid and oxygen or oxygen-containing gases, which contains noble metals of the 8th sub-group and/or compounds thereof, as well as optionally also gold and/or gold compounds, and as activators alkali metal compounds and/or alkaline earth metal compounds and/or cadmium compounds on a carrier, wherein the carrier consists of rods having a star-shaped cross section or of ribbed rods. Preference is given to rods with a star-shaped cross section.

For catalysis there are generally used carriers which consist of particles having large outer surfaces, for example spheres with an irregular surface, spheres with particles sintered onto the same, rods, cylinders, tablets and Raschig rings. These carrier catalysts show an increased efficiency as compared with the smooth spherical shape, which increase may be up to 20% in the case of Raschig rings. It was therefore to be expected that in the reaction of ethylene, acetic acid and oxygen to give vinyl acetate, an increased yield would be obtained by using carrier particles having a larger outer surface, such as Raschig rings. However, corresponding tests (Comparison Examples 1 to 4) showed that this is not the case. When Raschig rings were used, the yield was reduced as compared with spherical-shaped carrier particles; in the case of cylinder rods and tablets the same yield as for the spheres could be obtained, however, not without experiencing a pressure drop, which had a very unfavorable effect. It is very surprising that carriers which consist of rods having a star-shaped cross section—termed "star-rods" in the following—give a yield that is about twice as high as that of a spherical shaped carrier material, said yield being calculated in relation to the apparent density (=mass of 1 liter of poured carrier material) and thus to the amount of palladium employed. That is to say the apparent density of the star rods is only about half the apparent density of spherical-shaped carrier particles. This means that (with the same concentration of palladium in the individual carrier particle) there is only about half the amount of palladium in 1 liter of poured "star rod carrier" as compared with 1 liter of poured "spherical carrier". Nevertheless, the space-time yield (=amount of vinyl acetate formed per liter of poured carrier and per hour) is the same. Thus, the same space-time yield is achieved with half the amount of palladium. This is particularly surprising because the outer surface of star rods is smaller than that of spheres (both calculated on 1 liter of poured catalyst).

Besides, the pressure drop is even less significant in the case of "star rod carriers" than with "spherical carriers", which involves a saving of energy. The same is true for ribbed rods ("rib rods"). The star or rib rods may consist of all substances which have been known in literature as carrier materials for the vinyl acetate manufacture. Suitable carriers are, for example, silicic acid, silica gel, silicates (for example those of aluminum titanium, zirconium, beryllium, magnesium, or of rare earths), mixed silicates (such as clay minerals, feldspars), as well as aluminum oxides, spinels, titanium oxide, zirconium oxide, carbon in its different forms (such as activated charcoal, coke and graphite) and silicium carbide. However, preference is given to silicic acid, silica gel, spinels, aluminum silicates, clay minerals, aluminum oxide. Silicic acid is particularly preferred. The dimensions of the star or rib rods are preferably chosen in a way that on the one hand an easy charging of the carrier into the reactor is ensured (i.e. extremely large particles are excluded) and on the other hand there is no significant pressure drop (i.e. extremely small particles are excluded). The rods have generally a diameter of from 3 to 15 mm, preferably from 4 to 7 mm (calculated on the imaginary cylinder enclosing the rods). The stars have at least 3 and in general up to 15 points, the four- to six-pointed stars being preferred. The length of the rods is preferably smaller than the inner diameter of the reactor tube (or reactor tubes), in most cases it is in the range of from 4 to 20 mm, however, it may also be greater or smaller; preference is given to rods of a length of from 6 to 15 mm. The depth of the indentations and thus the diameter of the rod core should be chosen in a way that a sufficient mechanical strength is ensured. Generally this core has a diameter of from 2 to 4 mm. However, it may also be considerably shorter or wider in special cases. The shape of the star points and/or ribs may be angular or rounded.

Figure 1:
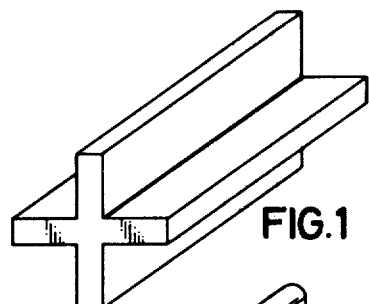
Figure 2:
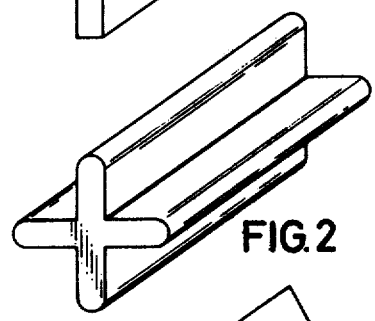

FIGS. 1 to 8 show some appropriate shapes:
FIG. 1: 4-pointed star rod with rectangular points
FIG. 2: 4-pointed star rod with rounded points
FIG. 3: 4-pointed star rod with triangular points
FIG. 4: 5-pointed star rod with triangular points
FIG. 5: 6-pointed star rod with triangular points
FIG. 6: 6-pointed star rod with toothed wheel points (ellipsoidic)
FIG. 7: 3-pointed star rod with angular points
FIG. 8: ribbed rod with rounded ribs.

Figure 3:
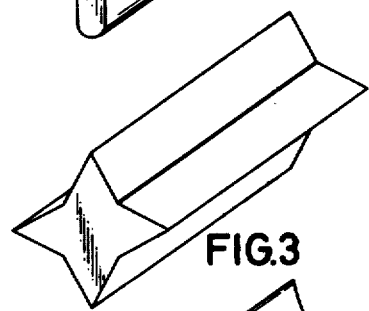
Figure 7:
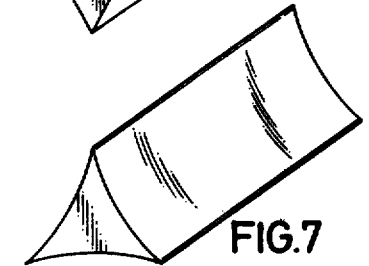
Figure 4:
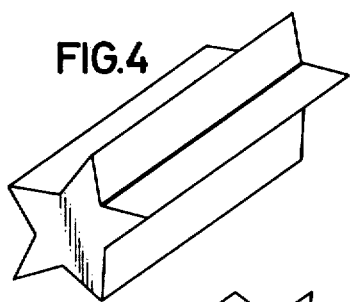
Figure 5:
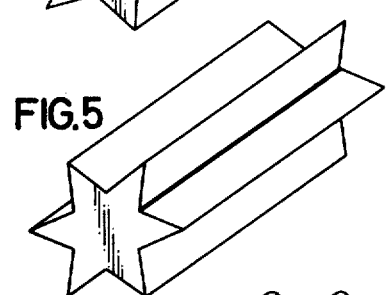
Figure 6:
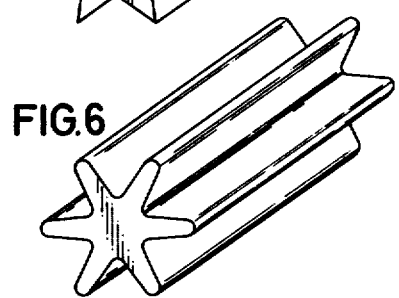

However, preference is given to triangular points (FIGS. 3, 4, 5).

The star or rib rods are manufactured in known manner by extrusion, pressing in a mould (pelleting press with a corresponding matrix) or casting. The extrusion process is preferred, however.

The catalytically active substances are applied onto the carrier in a known manner, for example by impregnating the carrier with a solution of the active substances and subsequently drying the same, and optionally by reduction. However, the active substances may also be applied, for example, by precipitating them onto the carrier by spraying, by vacuum coating or by dipping.

Suitable solvents for the catalytically active substances are above all unsubstituted carboxylic acids with up to 10 carbon atoms in the molecule, such as acetic acid, propionic acid, n- and iso-butyric acid and the various valeric acids. Due to its physical properties and also for economical reasons there is preferably used acetic acid as solvent. The additional use of an inert solvent is advantageous in cases where the substances are not sufficiently soluble in the carboxylic acid. Thus, for example, palladium chloride is far more soluble in aqueous acetic acid than in glacial acetic acid. As additional solvents there may be mentioned those which are inert and miscible with the carboxylic acid. Suitable are, for example, ketones such as acetone and acetyl acetone, and ethers such as tetrahydrofuran or dioxan, and also hydrocarbons such as benzene.

As compounds of noble metals of the 8th sub-group there may be used all salts and complex compounds which are soluble (as well as reducible, if required) and which do not leave any desactivating substances, such as halogen or sulfur, in the finished catalyst. Particularly appropriate are carboxylates, preferably the salts of aliphatic monocarboxylic acids with 2 to 5 carbon atoms as for example acetate, propionate or butyrate. Moreover, there are suitable, for example, nitrates, nitrites, oxide hydrates, oxalates, acetyl acetonates, acetoacetates. But also compounds such as sulfates and halides may be used, if care is taken that the sulfate radical or the halogen are removed prior to impregnation as by precipitation with barium acetate and silver nitrate, respectively, so that the sulfate or halogen anion does not get to the carrier. There is preferably used palladium in the form of its above-mentioned compounds. Due to its solubility and easy availability, palladium acetate is the specially preferred palladium compound.

The content of elements of the 8th sub-group in the catalyst is generally in the range of from 0.5 to 5% by weight, the percentage indicating the metal proportion being calculated on the total amount of the carrier catalyst.

Besides noble metals of the 8th sub-group and/or the compounds thereof, there may also be present gold and/or one of its compounds. A gold compound that is particularly appropriate is barium acetoaurate.

If gold and/or one of its compounds is used, it is generally added in a proportion of from 0.01 to 4% by weight, the percentage indicating the metal proportion being calculated on the total amount of the carrier catalyst.

As activators, alkali metal compounds and/or alkaline earth metal compounds and/or cadmium compounds are contained in the catalyst. There are suitable, for example, alkali metal carboxylates and alkaline earth metal carboxylates, such as potassium acetate, sodium acetate, lithium acetate, sodium propionate, calcium isobutyrate, magnesium acetate; there are also suitable those alkali metal or alkaline earth metal compounds which under the reaction conditions are converted into the carboxylates, such as hydroxides, oxides, or carbonates. As compounds of cadmium there are suitable those which do not contain halogen or sulfur, for example carboxylate (preferred), oxide, hydroxide, carbonate, citrate, tartrate, nitrate, acetyl acetonate, benzoyl acetonate, or acetoacetate. Cadmium acetate is particularly preferred. There may also be used mixtures of different activators. Each individual activator is generally added in a proportion of from 0.01 to 4% by weight, the percentage indicating the metal proportion of the activator being calculated on the total amount of the carrier catalyst.

The following catalysts are preferred: Palladium/alkali metal/cadmium and palladium/gold/alkali metal, wherein palladium and gold may be present as metals or compounds in the finished catalyst, with potassium being preferred as the alkali metal element (in the form of a carboxylate).

Preference is particularly given to the catalysts palladium acetate/potassium acetate/cadmium acetate and palladium acetate/barium acetoaurate/potassium acetate.

The impregnation of the catalyst carrier with the solution of the active components is preferably carried out by submerging the carrier material in the solution and thereafter eliminating the excess solution by pouring off or filtering off. With regard to solution losses it is advantageous to use only an amount of solution corresponding to the integral pore volume of the catalyst carrier and to mix the material thoroughly, so that all particles of the carrier material are uniformly wetted. This mixing may be achieved, for example, by stirring. It is advantageous to carry out the impregnating and the mixing simultaneously, as in a revolving drum or a tumbling drier, and the drying may be effected immediately afterwards. Furthermore it is recommended to employ the solution used for impregnating the catalyst carrier in such an amount and composition that it corresponds to the pore volume of the carrier material and that the intended amount of active substances is applied by a single impregnation step.

The drying of the catalyst carrier impregnated with the solution of the active substances is preferably effected under reduced pressure. It is furthermore generally recommended to carry out the drying in an inert gas current, for example in a nitrogen or carbon dioxide current. The residual content of solvent is preferably less than 8% by weight, preferably below 6% by weight.

If a reduction of the noble metal compounds (and the gold compounds, if any) is carried out, it may be effected in vacuo, at normal pressure or at elevated prssure up to 10 bars. In this case it is recommended to dilute the reducing agent with an inert gas to a higher extent with increased pressure. The reduction temperature is in the range of from 40° to 260° C., preferably between 70° and 200° C. Generally it is advantageous to use for the reduction a mixture of inert gas and reducing agent which contains from 0.01 to 50% by volume, preferably from 0.5 to 20% by volume, of reducing agent. As inert gas there may be used, for example, nitrogen, carbon dioxide, noble gases or paraffin hydrocarbons, such as methane, ethane, propane, isobutane and butane. Suitable reducing agents are, for example, hydrogen, methanol, formaldehyde, ethylene, propylene, isobutylene, butylene, and other olefins. The amount of reducing agent depends on the oxidation equivalent of the noble metal of the 8th sub-group and of the gold, if any; the reduction equivalent should be at least 1 to 1.5 times the oxidation equivalent, however, a greater amount of reducing agent has no adverse influence. For example, at least 1 mol of hydrogen should be used for 1 mol of palladium. The reduction may be effected following the drying in the same apparatus.

The preparation of vinyl acetate is generally effected by passing acetic acid, ethylene and oxygen or oxygen-containing gases at a temperature of from 100° to 250° C., preferably from 120° to 220° C., and at a pressure of from 1 to 25 bars, preferably from 1 to 20 bars, over the finished catalyst, in which process unreacted components may be recirculated. It is advantageous to choose the concentration conditions in a way that the reaction mixture is beyond the known explosion limits. The oxygen concentration is suitably maintained below 8% by volume (calculated on the gas mixture being free from acetic acid). However, a dilution with inert gases, such as nitrogen or carbon dioxide, is sometimes also advantageous. $CO_2$ is particularly suitable for dilution in cyclic processes, as it is formed in small amounts during the reaction.

The following Examples serve to illustrate the invention.

Comparison Example 1 (Spherical-shaped carrier particles)

5.0 l = 2550 g of a silicic acid carrier in spherical shape (sphere diameter of 6 mm) with a BET surface of 120 $m^2/g$, a bulk density of 0.53 kg/l and an outer surface of 0.81 $m^2/l$ (for definitions see the following Table) are impregnated with a solution of
  143 g of Pd acetate (47.3% of Pd)
  117 g of Cd acetate
  133 g of K acetate
in 1780 ml of glacial acetic acid and are dried at 60° C. under nitrogen at a pressure of 270 mbars.

4.5 Liters of catalyst are charged into a reaction tube having an inner width of 30 mm and a length of 7 m.

At a pressure of 9 bars (reactor inlet) and a catalyst temperature of from 175° to 178° C. a gas current of 20.25 $Nm^3/h$ is passed over the catalyst. Prior to being introduced into the reactor, the gas current consists of 60.8% by volume of ethylene, 15.5% by volume of inert gases ($N_2$ and $CO_2$), 17.4% by volume of acetic acid and 6.3% by volume of oxygen.

The results may be seen from the Table.

Comparison Example 2 (Cylinder-shaped carrier particles)

2200 g of $SiO_2$ cylindric rods having a diameter of 6 mm and an average length of 8 mm, a BET surface of 190 $m^2/g$, a bulk density of 0.44 kg/l and an outer surface of 1.47 $m^2/l$
are impregnated with a solution of
  124 g of Pd acetate
  100 g of Cd acetate
  115 g of K acetate
in 1800 ml of glacial acetic acid and are dried (as has been described in Comparison Example 1). The process is otherwise carried out as in Comparison Example 1. The results may be seen from the Table.

Comparison Example 3 (Carrier in tablet form)

2600 g of $SiO_2$ tablets having a cylindrical shape (diameter of 6 mm, height of 6 mm), a bulk density of 0.5 kg/l, a BET surface of 148 $m^2/g$ and an outer surface of 0.49 $m^2/l$
are impregnated with a solution of
  144 g of Pd acetate
  117 g of Cd acetate
  133 g of K acetate
in 1780 ml of glacial acetic acid and are dried (as has been described in Comparison Example 1). The process is otherwise carried out as in Comparison Example 1. The results may be seen from the Table.

Comparison Example 4 (Carrier in the form of Raschig rings)

2600 g of Raschig rings (outer diameter of 4 mm, inner diameter of 1.5 mm, height of 6 mm) of $SiO_2$ with a BET surface of 200 $m^2/g$, a bulk density of 0.5 kg/l, an outer surface of 0.98 $m^2/l$
are impregnated with a solution of
  144 g of Pd acetate
  117 g of Cd acetate
  133 g of K acetate
in 1025 ml of glacial acetic acid and are dried (as has been described in Comparison Example 1). The process is otherwise carried out as in Comparison Example 1. The results may be seen from the Table.

Example 1377 g of 5-pointed $SiO_2$ star rods having a depth of indentation of 1.7 mm, a diameter of 6 mm (properly speaking this is the diameter of the imaginary closest cylinder which surrounds the star rods), an average length of 8 mm, a bulk density of 0.27 kg/l, an outer surface of 0.74 $m^2/l$, a BET surface of 190 $m^2/g$
are impregnated with a solution of
  78 g of Pd acetate
  62 g of Cd acetate
  73 g of K acetate
in 1583 ml of glacial acetic acid and are dried (as has been described in Comparison Example 1). The process is otherwise carried out as in Comparison Example 1. The results may be seen from the Table.

After the drying, all five catalysts prepared contain
  2.3% of $Pd^{++}$
  1.7% of $Cd^{++}$
  1.9% of $K^+$
in the form of the acetates.

|  | Comparison Example 1 Spheres | Comparison Example 2 Cylinder rods | Comparison Example 3 Tablets | Comparison Example 4 Raschig rings | Example Star rods |
|---|---|---|---|---|---|
| 1. BET surface | 120 $m^2/g$ | 190 $m^2/g$ | 148 $m^2/g$ | 200 $m^2/g$ | 190 $m^2/g$ |
| 2. Outer surface | 0.81 $m^2/l$ | 1.47 $m^2/l$ | 0.49 $m^2/l$ | 0.98 $m^2/l$ | 0.74 $m^2/l$ |
| 3. Bulk density | 0.53 kg/l | 0.44 kg/l | 0.50 kg/l | 0.50 kg/l | 0.27 kg/l |
| 4. Palladium content | 13.5 g/l | 11.7 g/l | 13.6 g/l | 13.6 g/l | 7.3 g/l |

-continued

|   | Comparison Example 1 Spheres | Comparison Example 2 Cylinder rods | Comparison Example 3 Tablets | Comparison Example 4 Raschig rings | Example Star rods |
|---|---|---|---|---|---|
| 5. STY | 1050 g/l · h | 1015 g/l · h | 1040 g/l · h | 872 g/l · h | 1067 g/l · h |
| 6. Specific yield | 77.8 g | 86.8 g | 76.5 g | 64.1 g | 146.2 g |
| 7. Pressure drop | 0.31 bar/m | 0.36 bar/m | 0.49 bar/m | 0.26 bar/m | 0.23 bar/m |

1. The "BET surface" is measured according to the method of Brunauer, Emmett and Teller and indicates the total surface of 1 gram of carrier material (i.e. the sum of the outer surface plus the surface of all open pores).
2. The "outer surface" of the carrier is the surface of 1 liter of poured carrier material, without considering the surface of the pores. This value is calculated on the basis of the number of carrier particles in 1 liter of poured carrier material and the geometrical surface of the individual carrier particle.
3. The "bulk density" is the mass of 1 liter of poured carrier material.
4. The "palladium content" is the amount of palladium in 1 liter of poured carrier material.
5. "STY" is the space-time yeild, i.e. the amount of final product per liter of poured carrier material and per hour.
6. The "specific yield" is the amount of vinyl acetate per gram of palladium and per hour.

What is claimed is:

1. An improved catalyst for the preparation of vinyl acetate in the gaseous phase from ethylene, acetic acid and oxygen or oxygen-containing gases of the type containing as an active component a noble metal of subgroup VIII optionally in admixture with gold and/or a compound thereof and an activator of an alkali metal compound and/or an alkaline earth metal compound and/or a cadmium compound wherein said active component is applied onto a carrer, wherein the improvement comprises a carrier consisting essentially of either ribbed rods or rods with a star-shaped cross section.

2. A catalyst as claimed in claim 1, wherein the cross section of the rods represent a 4- to 6-pointed star.

3. A catalyst as claimed in claims 1 or 2, wherein the carrier consists of silicic acid.

* * * * *